United States Patent [19]
Sholder

[11] Patent Number: 5,476,487
[45] Date of Patent: Dec. 19, 1995

[54] AUTOTHRESHOLD ASSESSMENT IN AN IMPLANTABLE PACEMAKER

[75] Inventor: Jason A. Sholder, Beverly Hills, Calif.

[73] Assignee: Pacesetter, Inc., Sylmar, Calif.

[21] Appl. No.: 365,278

[22] Filed: Dec. 28, 1994

[51] Int. Cl.⁶ .................................................. A61N 1/37
[52] U.S. Cl. ................................................... 607/28
[58] Field of Search ........................ 607/28, 11, 25, 607/27

[56] References Cited

U.S. PATENT DOCUMENTS

| | | | |
|---|---|---|---|
| 4,228,803 | 10/1980 | Richards | 128/419 PG |
| 4,556,062 | 12/1985 | Grassi et al. | 128/419 PG |
| 4,674,508 | 6/1987 | DeCote | 128/419 PT |
| 4,674,509 | 6/1987 | DeCote, Jr. | 128/419 PT |
| 4,686,988 | 8/1987 | Sholder | 607/28 |
| 4,708,142 | 11/1987 | DeCote, Jr. | 128/419 PT |
| 4,729,376 | 3/1988 | DeCote, Jr. | 128/419 PT |
| 4,858,610 | 8/1989 | Callaghan et al. | 128/419 PG |
| 4,913,146 | 4/1990 | DeCote, Jr. | 128/419 PG |
| 5,161,529 | 11/1992 | Stotts et al. | 128/419 PG |
| 5,222,493 | 6/1993 | Sholder | 128/419 P |
| 5,350,410 | 9/1994 | Kleks et al. | 607/28 |

Primary Examiner—William E. Kamm
Assistant Examiner—Kennedy J. Schaetze
Attorney, Agent, or Firm—Lisa P. Weinberg

[57] ABSTRACT

Capture is assessed in an implantable pacemaker by issuing a pair of stimulation pulses, separated by about 60–100 milliseconds. The second pulse of the stimulation pair is set to an energy level that assures capture, and remains at that level. The first pulse of the stimulation pair is initially set to an energy level that assures capture, and its energy level is thereafter systematically decreased, e.g., its amplitude is decreased, by a set amount each time the pair of stimulation pulses is issued. One of the stimulation pulses of the stimulation pair will always cause capture: the first pulse when its energy level is greater than the capture threshold (in which case the second pulse is issued into refractory cardiac tissue and has no effect); or the second pulse, when the energy of the first pulse drops below the capture threshold. In either event, a T-wave follows the capturing pulse, whether the first or the second, evidencing repolarization of the cardiac tissue. Capture is assessed by measuring the time interval between a fixed reference point associated with the stimulation pair, e.g., the first pulse, and the T-wave. A significant change in this time interval, e.g., of approximately 60–100 milliseconds, indicates that the first pulse has dropped below the capture threshold.

20 Claims, 8 Drawing Sheets

AUTOTHRESHOLD ASSESSMENT IN AN IMPLANTABLE PACEMAKER

BACKGROUND OF THE INVENTION

FIELD OF THE INVENTION

The present invention relates to implantable medical devices and methods, and more particularly to an implantable pacemaker or pacemaker system that provides a simple and easy-to-implement technique for automatically assessing the capture threshold ("autothreshold") of the implantable pacemaker. Once the capture threshold is known, the stimulus energy may then be automatically adjusted as needed in order to assure that the output stimulus effectuates capture ("autocapture").

It is anticipated that pacemakers will soon employ autocapture and autothreshold features that enable the capture threshold of a given patient to be regularly determined, thereby enabling the output energy of the pacer stimulus to be optimally set to a value that is above the capture threshold, but not too far above the capture threshold. Assuring that the output energy is above threshold assures that capture will occur, while keeping the output energy not too far above threshold conserves the limited power available within the pacemaker battery.

Reliably determining capture within an implantable pacer has heretofore been a formidable task. "Capture" occurs when the applied electrical stimulus generated by the pacemaker is of sufficient energy to stimulate or depolarize the cardiac muscle tissue, thereby causing a cardiac contraction. Capture fails to occur when the applied stimulus is of insufficient energy to stimulate or depolarize the cardiac tissue. Needless to say, for a cardiac pacemaker to properly perform its intended function, it is critically important that the electrical stimuli it issues be of sufficient energy to capture the heart, i.e., to cause the cardiac tissue to depolarize.

The classical approach to determine capture is to apply a ventricular stimulus (V-pulse) to the ventricle of the heart and look for an evoked R-wave response with each and every V-pulse thus applied. The evoked R-wave response is usually monitored between the tip and ring of a bipolar lead connected to the pacemaker sensing circuits. The evoked R-wave response may also be monitored by looking between the ring electrode and pacemaker case. In either event, a bipolar pacing lead has generally been required in order to detect the evoked response.

The evoked R-wave response is monitored immediately (within 5-20 msec) of the pacing pulse (V-pulse) at a time when the polarization voltage, i.e., that voltage which appears at an electrode/tissue interface when an electrical stimulus is applied to tissue through the electrode, is relatively high. In order to avoid detecting the polarization voltage and classifying it as an evoked R-wave response, it is necessary to use low polarization materials in the electrode. Further, a calibration algorithm is typically needed in order to set an evoked R-wave response threshold voltage since the evoked R-wave response and polarization voltage occur simultaneously. Thus, when the polarization voltage is very high, it may not be possible to reliably detect an evoked R-wave response.

Assuming that an evoked R-wave response can be detected, a high output backup pulse may be applied when no evoked R-wave response from a primary pacer pulse is detected (i.e., when loss of capture occurs). Should two (2) consecutive loss-of-capture events occur, an autocapture routine of the pacer then incrementally increases the amplitude of the primary stimulus until capture occurs as determined by detecting an evoked R-wave response from the new increased-energy primary stimulus.

An autothreshold algorithm may also be periodically invoked, e.g., once or twice a day, during which the pacer decrements the amplitude of its output stimulus until capture is lost (no evoked response). The output is then incrementally increased until capture is regained. Every loss of capture primary stimulus is followed by a high output back-up stimulus in order to maintain the cardiac rhythm of the patient.

All prior art autocapture and autothreshold schemes require a bipolar pacing system, or at least a bipolar sensing configuration. It has thus not heretofore been possible to reliably provide the autocapture and autothreshold features when only monopolar pacing is employed. Further, autocapture and/or autothreshold may not work with all pacing leads (i.e., leads that exhibit high polarization potentials). Additionally, verifying capture with every pacing pulse may require significant overhead in the pacing circuitry in order to assure that a polarization voltage is not incorrectly detected as an evoked R-wave response.

What is needed, therefore, is an improved way to reliably assess the capture threshold. In particular, what is needed is a capture-assessment technique that does not require the evoked R-wave response to be sensed, and that thus eliminates the problems associated with distinguishing the evoked R-wave response from polarization voltages, and avoids the need of using low polarization materials in the electrode.

SUMMARY OF THE INVENTION

The present invention addresses the above and other needs by providing an implantable pacemaker wherein capture is assessed by issuing a pair of stimulation pulses, separated in time by amount less than the refractory period of the cardiac tissue, e.g., about 60–100 milliseconds. The second pulse of the stimulation pair is always set to an energy level that has a high probability of causing capture, e.g., at the maximum energy level, and remains at that level. In a preferred embodiment, the first pulse of the stimulation pair is also initially set to an energy level that has a high probability of causing capture, e.g., to the same energy level as the second pulse of the pair, and its energy level is thereafter systematically decreased. For example, after initially generating two or three pairs of pulses having a fixed amplitude, the amplitude of the first pulse of the pair may be decreased by a set amount each time (or every other time) the pair of stimulation pulses is issued. One of the stimulation pulses of each stimulation pair will always cause capture: (1) the first pulse when its energy level is greater than the capture threshold (in which case the second pulse is issued into refractory cardiac tissue and has no effect); or (2) the second pulse, when the energy of the first pulse drops below the capture threshold. In either event, a T-wave follows the capturing pulse, whether the capturing pulse is the first pulse or the second pulse, evidencing repolarization of the cardiac tissue.

Advantageously, the T-wave occurs at a time following the capturing pulse when polarization voltages are no longer present at the electrode/tissue interface. The capture threshold is thus assessed by measuring the time interval between a fixed reference point associated with the stimulation pair, e.g., the first pulse, and the T-wave. A significant change in this time interval, e.g., of at least 20% or approximately 60–100 milliseconds, indicates that the first pulse has dropped below the capture threshold.

Thus, the present invention advantageously determines capture or lack-of-capture by simply measuring the stimulus-to-T-wave time period rather than looking for an evoked response immediately following application of the stimulus. Advantageously, by measuring the stimulus-to-T-wave time rather than looking for an evoked response immediately following an applied stimulus, the problems associated with the relatively high polarization voltages at the electrode-tissue interface are eliminated.

The T-wave is preferably sensed using an intracardiac electrogram (IEGM) amplifier that is separate from the standard sense amplifier. Such IEGM amplifier senses activity between the tip electrode and the pacer case. Thus, either a bipolar or unipolar lead or pacing configuration may be used for this purpose.

The invention may be broadly viewed as a method of automatically assessing a capture threshold of an implantable pacemaker that is electrically coupled to cardiac tissue. To practice the method the pacemaker must include means for generating a sequence of electrical stimuli, where each stimulus of the sequence has a controlled energy content, and means for measuring time intervals. The method comprises: (a) generating a sequence of paired stimuli at a prescribed pacing rate, with a leading stimulus of each pair of the paired stimuli having an adjustable energy content beginning with an energy content above or below the capture threshold, and a trailing stimulus of each pair of the paired stimuli always having an energy content above the capture threshold; (b) applying the sequence of paired stimuli to the cardiac tissue while adjusting the energy content of the leading stimulus towards the capture threshold; (c) measuring how long it takes the cardiac tissue to repolarize from a fixed reference point associated with the paired stimuli; and (d) assessing the capture threshold to be approximately equal to the energy content of the leading stimulus of the paired stimuli that immediately precedes a substantial change in the repolarization time.

In such method, the leading stimulus of each pair should be separated from the trailing stimulus of each pair by a fixed amount, usually 60 to 100 milliseconds. It is this separation time in the stimuli of each pair that gives rise to the "substantial change" that occurs in the measured time to the occurrence of a T-wave, which time may be referred to as a "repolarization time". Note, however, that "repolarization time", as used here, is not necessarily the "physiological repolarization time", but is the time measured from a fixed reference point associated with the paired stimuli, e.g., the first pulse, and the occurrence of a T-wave. Should the fixed reference point be the first pulse, and should the first pulse be the pulse that causes capture, then the measured "repolarization time" is the true physiologic repolarization time. Because the physiologic repolarization time (capturing-stimulus-to-T-wave time) is usually 200–300 milliseconds, the "substantial change" in the measured repolarization time will usually be a change of at least 20%.

It should be noted from the broad description of the method of the invention above that the invention is not limited to being practiced in just the ventricle. As a practical matter, it usually will be practiced in the ventricle because the T-wave provides a convenient signal that allows the ventricular repolarization time to be measured. However, should a way be developed to measure the atrial repolarization time, then the invention could be used just as easily to assess atrial capture thresholds.

Note also from the above broad description that the leading stimulus of the stimuli pair may initially be either below or above the capture threshold. As a practical matter, it will usually be set to an initial value that is above the capture threshold, e.g., equal to the trailing stimulus, but it need not be. All that is important for purposes of the invention is that the energy of the leading stimulus be systematically adjusted, e.g., incrementally adjusted each time the stimuli pair is generated, in a direction that will eventually cause it to cross over the capture threshold. When such cross over occurs, there will be a substantial change in the measured "repolarization time".

The present invention may also be characterized as a capture threshold assessment system for use within an implantable pacemaker. The system includes (a) a paced interval timer; (b) a pulse generator responsive to the paced interval timer; (c) a sense amplifier that senses T-waves; (d) a stop timer that measures time intervals; (e) a time comparison circuit; and (f) a loss-of-capture signal generator responsive to the time comparison circuit.

In operation, the paced interval timer defines a paced interval. When the capture threshold is to be assessed, the pulse generator generates a pair of stimulation pulses in synchrony with the paced interval. A first pulse of the pair has a first programmed amplitude, and a second pulse of the pulse pair has a second programmed amplitude, with both the first programmed amplitude being initially set to a known value, e.g., a value that causes capture, and with the second programmed amplitude being set to a value that is known to cause capture, and with the first pulse amplitude being systematically changed thereafter. The first and second pulses are separated by a time period $t_S$, where $t_S$ is less than the refractory period of the cardiac tissue. The time period $t_S$ will usually be about 60–100 msec. The sense amplifier senses the T-wave that occurs as a result the pair of stimulation pulses, one of which stimulation pulses will always cause capture. The stop timer measures the time interval within each paced interval that starts when the pulse generator generates one of the stimulation pulses (a fixed reference point) and stops when the sense amplifier senses a T-wave. The time interval thus measured provides a measure of how long it takes a T-wave to occur in each paced interval following the fixed reference point of the pulse pair. The time comparison circuit simply compares the time interval measured by the stop timer against a reference time interval, where the reference time interval defines a nominal delay between a stimulation pulse that causes capture and the T-wave resulting from such capture. The loss-of-capture signal generator then generates a loss-of-capture signal whenever the time interval measured by the stop timer differs from the reference time interval by an amount approximately equal to $t_S$.

It is a feature and advantage of the present invention to provide an implantable pacemaker wherein capture can be assessed without the need to sense an evoked response immediately following an applied stimulus, and at a time when potentially interfering polarization voltages are not present at the electrode/tissue interface.

It is another feature and advantage of the invention to provide a simple capture-determining technique that does not require bipolar pacing leads, nor special low-polarization electrode materials.

It is a further feature of the invention to provide a pacing system wherein an autothreshold feature is regularly and automatically invoked that reliably detects the capture threshold, and wherein an autocapture feature may be selectively triggered thereafter to set the stimulus energy at a level that is above the determined capture threshold by a prescribed safety margin.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
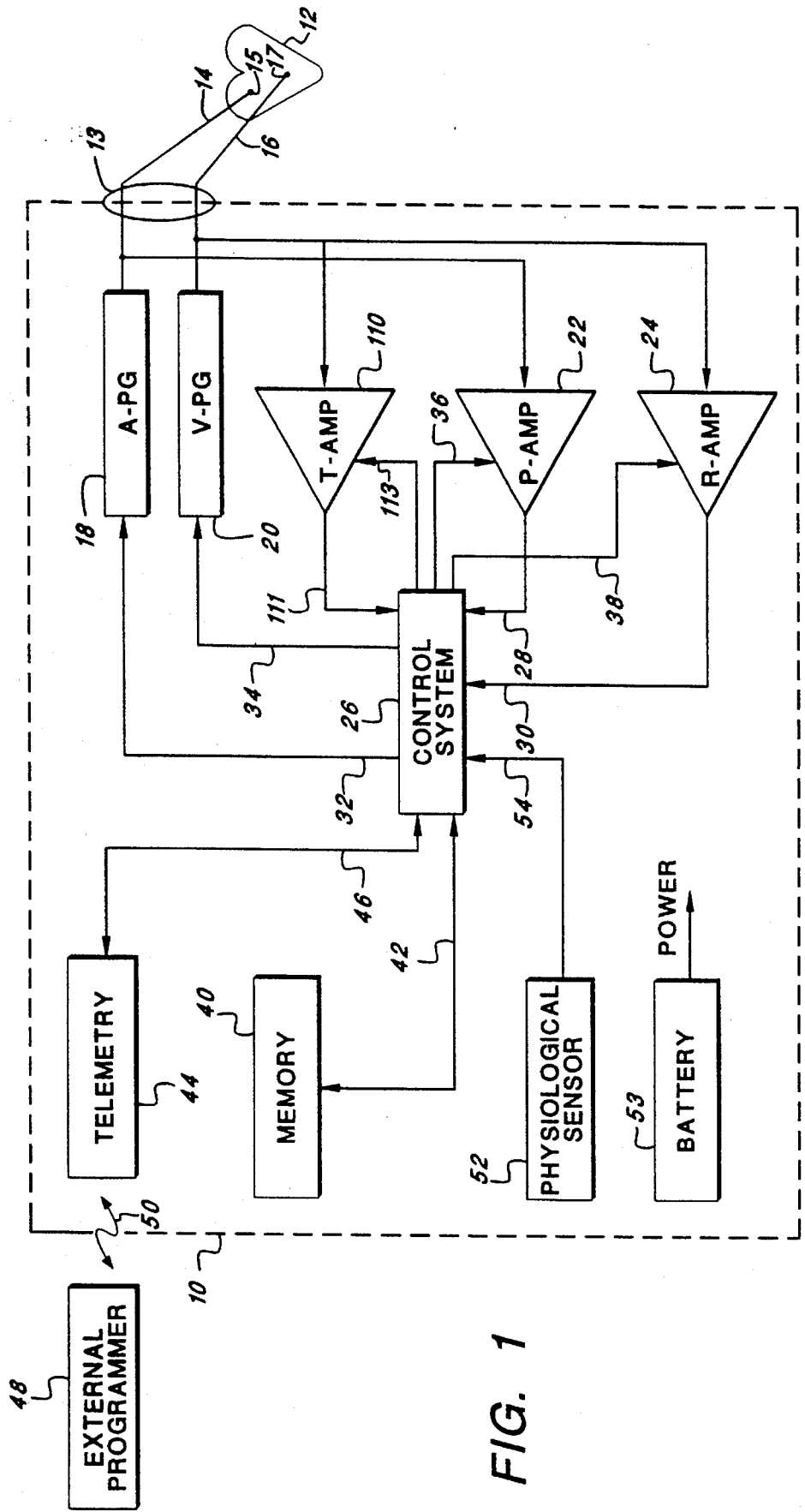
FIG. 1 is block diagram of a representative pacemaker with which the present invention could be used.

The present invention is intended for use within an implantable pacemaker. A functional block diagram of a representative pacemaker with which the present invention may be used is illustrated in FIG. 1. As seen in FIG. 1, a pacemaker 10 is coupled to a heart 12 by way of leads 14 and 16. (Note, in subsequent figures, e.g., FIG. 6, the leads 14 and 16 are referred to as the lead system 19.) The lead 14 has an electrode 15 that is in contact with one of the atria of the heart, and the lead 16 has an electrode 17 that is in contact with one of the ventricles of the heart. The leads 14 and 16 carry electrical stimulating pulses (stimuli) to the electrodes 15 and 17 from an atrial pulse generator (A-PG) 18 and a ventricular pulse generator (V-PG) 20, respectively. Further, electrical signals from the atria are carried from the electrode 15, through the lead 14, to the input terminal of an atrial channel sense amplifier (P-AMP) 22; and electrical signals from the ventricles are carried from the electrode 17, through the lead 16, to the input terminal of a ventricular sense channel amplifier (R-AMP) 24. In addition, in accordance with the present invention, as explained more fully below, a T-wave amplifier (T-AMP) 110 is used to sense T-waves in the ventricles.

Controlling the dual-chamber pacer 10 is a control circuit or control system 26. The control system 26 receives the output signals from the atrial amplifier 22 over signal line 28. Similarly, the control system 26 receives the output signals from the ventricular amplifier 24 over signal line 30, and output signals from the T-wave amplifier 110 over signal line 111. The output signals on signal lines 28 and 30 are generated each time that a P-wave or an R-wave is sensed within the heart 12. Similarly, an output signal on signal line 111 is generated each time that a T-wave is sensed within the ventricle of the heart 12. The control circuit or system 26 also generates trigger signals that are sent to the atrial pulse generator 18 and the ventricular pulse generator 20 over signal lines 32 and 34, respectively. These trigger signals are generated each time that a stimulation pulse is to be generated by the respective pulse generator 18 or 20. A stimulation pulse generated by the A-PG 18 is referred to as the "A-pulse," and the stimulation pulse generated by the V-PG 20 is referred to as the "V-pulse." For purposes of the present invention, as explained below, the V-PG 20 generates a pair of V-pulses whenever the pacemaker 10 is operating in an autothreshold mode, i.e., a mode wherein capture threshold of the heart 12 is to be assessed. During the time that either an A-pulse or V-pulse is being delivered to the heart, the corresponding amplifier, P-AMP 22 and/or R-AMP 24, and the T-AMP 110, is typically disabled by way of a blanking signal presented to these amplifiers from the control system over signal lines 36, 38, and 113 respectively. This blanking action prevents the amplifiers 22, 24 and 110 from becoming saturated from the relatively large A-pulse or V-pulse, respectively, that is present at the input terminals of such amplifiers during this time. Such blanking action also helps prevent residual electrical signals present in the muscle tissue as a result of the pacer stimulation from being interpreted as P-waves or R-waves.

Still referring to FIG. 1, the pacer 10 also includes a memory circuit 40 that is coupled to the control system 26 over a suitable data/address bus 42. The memory circuit 40 allows certain control parameters, used by the control system 26 in controlling the operation of the pacemaker, to be programmably stored and modified, as required, in order to customize the pacer's operation to suit the needs of a particular patient. Such data includes the basic timing intervals used during operation of the pacemaker, such as a programmed atrial escape interval (AEI). For purposes of the present invention, such data may also include energy (amplitude) data used to initially set and/or systematically decrease the V-pulses during the autothreshold operation, as well as a safety factor that specifies how much above the measured capture threshold the stimulus energy should be set, as explained more fully below. Further, data sensed during the operation of the pacer may be stored in the memory 40 for later retrieval and analysis, such as the measured capture threshold.

A telemetry circuit 44 is further included in the pacer 10. This telemetry circuit 44 is connected to the control system 26 by way of a suitable command/data bus 46. In turn, the telemetry circuit 44, which is included within the implantable pacer 10, may be selectively coupled to an external programming device 48 by means of an appropriate communication link 50, which communication link 50 may be any suitable electromagnetic link, such as an RF (radio frequency) channel. Advantageously, through the external programmer 48 and the communication link 50, desired commands may be sent to the control system 26. Similarly, through this communication link 50 and the programmer 48, data (either held within the control system 26, as in a data latch, or stored within the memory 40), may be remotely received from the pacer 10. In this manner, noninvasive communications can be established from time to time with the implanted pacer 10 from a remote, non-implanted location. Many suitable telemetry circuits known in the art that may be used with the present invention for the telemetry circuit 44. See, e.g., U.S. Pat. No. 4,847,617.

The pacer 10 in FIG. 1 is referred to as a dual-chamber pacemaker because it interfaces with both the atria and the ventricles of the heart. Those portions of the pacer 10 that interface with the atria, e.g., the lead 14, the P-wave sense amplifier 22, the A-pulse generator 18, and corresponding portions of the control system 26, are commonly referred to as the atrial channel. Similarly, those portions of the pacer 10 that interface with the ventricles, e.g., the lead 16, the R-wave sense amplifier 24, the T-wave amplifier 110, the V-pulse generator 20, and corresponding portions of the control system 26, are commonly referred to as the ventricular channel. It is to be emphasized, however, that the autothreshold assessment capability of the present invention is not restricted to use with only dual-chamber pacemakers, but may also be used with single chamber pacemakers, i.e., pacemakers that sense and pace in only one chamber of the heart. Indeed, the ability to use the invention with either a single chamber or dual chamber pacemaker is one of the advantages of the invention.

In some pacemakers that implement the present invention, the pacemaker 10 will include one or more physiological sensors 52 that is/are connected to the control system 26 of the pacer over a suitable connection line 54. While the sensor 52 is illustrated in FIG. 1 as being included within the pacer 10, it is to be understood that the sensor may also be external to the pacer 10, yet still be implanted within or carried by the patient. A common type of sensor is an activity sensor, such as a piezoelectric crystal, mounted to the case of the pacemaker. Other types of physiologic sensors, such as sensors that sense the oxygen content of blood, respiration rate, pH of blood, body motion, and the like, may also be used in lieu of, or in addition to, an activity sensor. The type of sensor, if any, used is not critical to the present invention. Any sensor, or combination of sensors, capable of sensing a physiological parameter relatable to the rate at which the heart should be beating can be used. A pacemaker using such sensor(s) is commonly referred to as a "rate-responsive" (RR) pacemaker because such a pacemaker adjusts the rate (the basic pacing interval or escape interval) of the pacer in a manner that tracks the physiological needs of the patient.

It is noted that the control system 26 of the pacemaker may take numerous forms, any of which is suitable for purposes of the present invention. The details of the control system 26, whether based on a microprocessor, state machine, or other type of control devices, or simulated control devices, are not critical to an understanding or implementation of the present invention, and hence are not presented herein. Such details may be found in the literature, if desired. See, e.g., U.S. Pat. No. 4,712,555 wherein a state-machine type of operation for a pacemaker is described; U.S. Pat. No. 4,788,980, wherein the various timing intervals used within the pacemaker and their interrelationship are more thoroughly described; and U.S. Pat. No. 4,944,298 wherein an atrial-rate based programmable pacemaker is described. The '555, '980, and '298 patents are incorporated herein by reference. All that is important for purposes of the present invention, as explained fully below, is that the control system of the pacemaker be capable, in conjunction with other pacemaker circuitry, of measuring the time interval between one of the V-pulses of a pair of V-pulses issued during an autothreshold mode, at least one of which will always capture the heart, and thus cause a T-wave to occur, and the T-wave thus caused by the pair of V-pulses.

Figure 2:
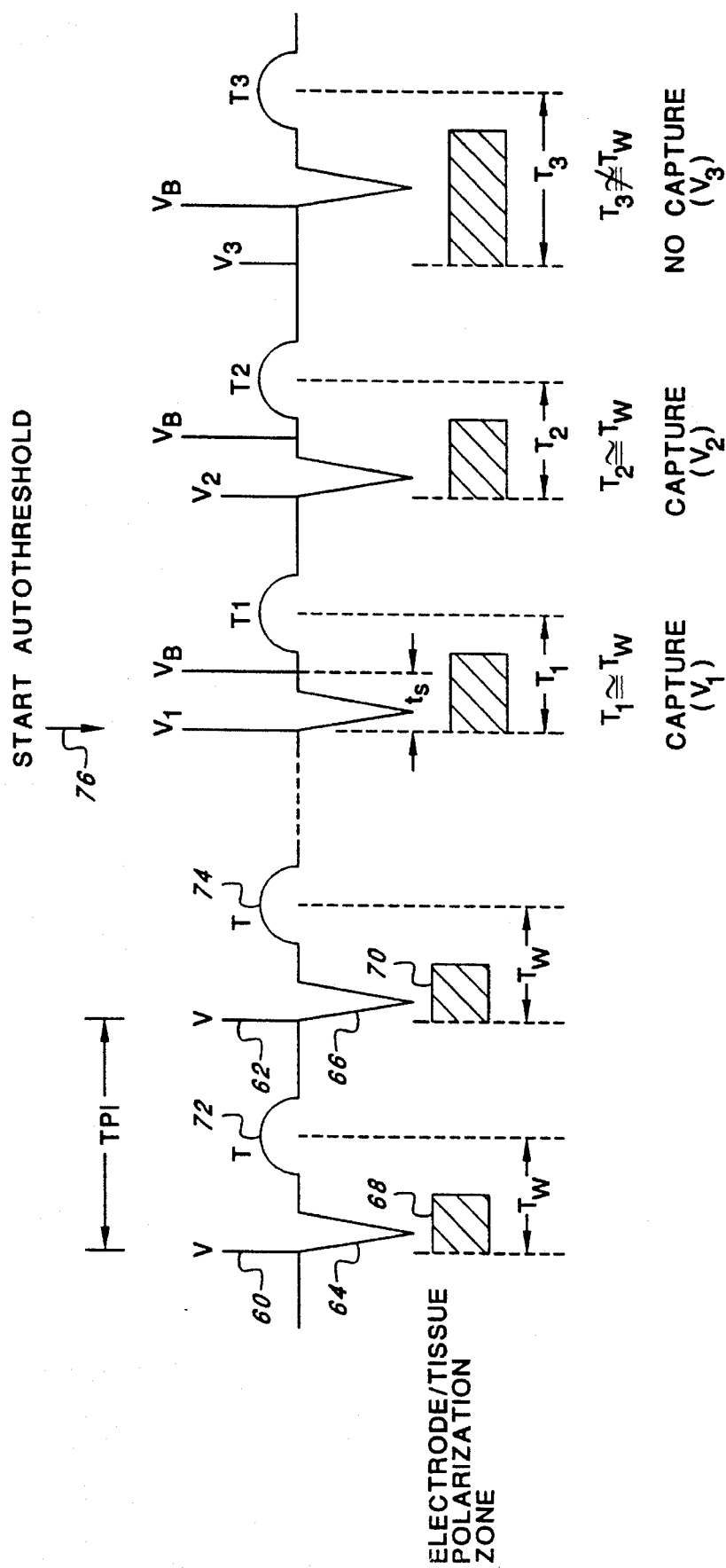
FIG. 2 is a timing waveform diagram that conceptually illustrates how the present invention determines the capture threshold.

Referring next to FIG. 2, there is shown a timing waveform diagram that conceptually illustrates how the present invention automatically assesses or determines the capture threshold. The diagram of FIG. 2 depicts key cardiac events that occur during a ventricular pacing cycle. The cardiac events illustrated in FIG. 2 appear as such events might appear in an intracardiac electrogram (IEGM), with time being represented along the horizontal axis. Thus, the pacing cycle, for purposes of FIG. 2, is defined as the time interval $T_{PI}$ between ventricular stimuli, i.e., the time interval between a first V-pulse 60 and a second V-pulse 62. For a heart paced to beat at a rate of 60 beats per minute (bpm), the time interval $T_{PI}$ would thus be 1000 milliseconds (1 second). (Note: atrial events, e.g., P-waves and/or A-pulses are not depicted in FIG. 2.)

As depicted in FIG. 2, each V-pulse 60 and 62 is of sufficient energy to capture the cardiac tissue. Hence, immediately following each V-pulse 60 and 62, there is an evoked R-wave 64 and 66, respectively. The R-wave represents depolarization of the ventricular muscle tissue. Depolarization of the muscle tissue, in turn, causes the ventricular tissue to physically contract, thereby pumping blood (which is, of course, the function of the heart—to pump blood). It is thus seen that when a V-pulse captures the heart, it causes the ventricle of the heart to contract, and thereby forces the heart to beat—pump blood—at a set rate.

Also shown in FIG. 2, is a period of time, or "window" of time, referred to as the electrode/tissue polarization zone. It is during this zone, e.g., the zone 68 following V-pulse 60, and the zone 70, following V-pulse 62, that a polarization voltage is likely to be present at the electrode/tissue interface. Such polarization voltage, as has been indicated, complicates the process of trying to detect the evoked response, e.g., the R-wave 64 or the R-wave 66. The polarization voltage thus represents an obstacle that interferes with accurately assessing whether or not capture has occurred. Advantageously, the present invention avoids the problems associated with the polarization voltage by not detecting an evoked response during the polarization zone.

As further seen in FIG. 2, following the delivery of a capturing V-pulse 60 or 62, a T-wave 72 or 74, respectively, occurs. A T-wave always follows a depolarization of the cardiac tissue. The T-wave evidences the repolarization of the ventricular tissue. (Note, although atrial activity is not included in FIG. 2, it is noted that when atrial tissue is depolarized, e.g., by an atrial stimulation pulse, or A-pulse, it also repolarizes. Usually, there is no detectable wave within the IEGM evidencing such atrial repolarization because it is masked out by the R-wave.) During the time period that follows depolarization up until the time when the T-wave occurs in the cardiac pacing cycle, the ventricular muscle tissue is refractory, i.e., it is incapable of contracting because it is just recovering from a depolarization/contraction. The time interval from the evoked response R-wave 64 or 66 until the occurrence of the T-wave 68 or 70 thus comprises a repolarization time. Assuming that an applied V-pulse captures the ventricles, this repolarization time interval will thus be approximately equal to the time interval between the V-pulse and the resulting T-wave. Such time interval is depicted in FIG. 2 as the time $T_W$.

In accordance with the present invention, an autothreshold mode is used to assess or define the capture threshold. In FIG. 2, the autothreshold mode begins by applying a sequence of V-pulses, $V_i$, of decreasing energy, each being followed by a high energy back-up stimulus, $V_B$, and measuring the time interval, $T_i$, between the $V_i$ pulse and the following T-wave. Each pair of V-pulses in the sequence thus comprises a primary V-pulse, $V_i$, followed by a backup pulse, $V_B$. The autothreshold mode thus starts with a first primary V-pulse $V_1$, at a time 76. The backup stimulus, $V_B$, follows the primary stimulus, $V_i$, by a time $t_S$, where $t_S$ is typically 60 to 100 msec (a time period which is less than the natural refractory period of the heart). The backup stimulus, $V_B$, has sufficient energy, e.g., is of sufficient amplitude, to assure capture. The primary stimulus $V_i$ also starts at an energy that is sufficient to cause capture. E.g., the primary stimulus $V_i$ may be initially set to the same amplitude as the backup stimulus, $V_B$. When the primary stimulus $V_i$ captures the heart, then the backup stimulus, $V_B$, is issued into the heart while it is refractory and causes no harm. Should the primary stimulus $V_i$ not be sufficient energy to effectuate capture, then the backup stimulus $V_B$ will capture the heart. In either event, the T-wave occurs at a time, $T_W$, following the capturing stimulus. Hence, by applying a sequence of $V_i$-$V_B$ pulse pairs to the heart, where each $V_i$ pulse has a reduced energy from the $V_{i-1}$ pulse of the prior pulse pair, and by measuring the time interval $T_i$ between the $V_i$ pulse and the following T-wave, which time interval $T_i$ will be approximately equal to $T_W$ if the $V_i$ pulse has caused capture, but will be substantially longer than $T_W$ if the $V_i$ pulse has not caused capture, the capture threshold can readily be determined.

As seen in FIG. 2, a nominal (average) stimulus-to-T-wave time interval $T_W$ may first be determined by monitoring a prescribed number, e.g., 3–10, of paced cardiac cycles, measuring $T_W$ (time interval from the V-pulse to the T-wave) for each cycle, and averaging the values of $T_W$ thus measured. This determination of $T_W$ is preferably performed while the patient is at rest and the heart rhythm is stable.

Once the nominal or average $T_W$ is known, the autothreshold routine begins, at 76, by issuing a first pair of stimulation pulses: $V_1$, followed by a backup stimulation pulse, $V_B$, some 60–100 msec later. The time interval from the primary V-pulse, $V_1$, of the pulse pair to the resulting T-wave (shown as $T_1$ in FIG. 1), is measured. For the situation shown in FIG. 2, the first pulse, $V_1$, of the first stimulation pair effectuates capture, and the measured time interval $T_1$ will thus be approximately equal to the predetermined value of $T_W$. A second pair of stimulation pulses is then issued: $V_2$ followed by a backup pulse $V_B$, with $V_2$ having an energy (amplitude) that is less than that of $V_1$. The primary V-pulse-to-T-wave time interval is again measured, and found to be approximately equal to $T_2$ ($=T_W$), indicating that the pulse $V_2$ was the ventricular stimulus of the pulse pair that caused capture. A third pair of stimulation pulses is next issued: $V_3$ followed by a backup pulse $V_B$, with $V_3$ having an energy (amplitude) that is less than that of $V_2$. The V-pulse-to-T-wave time interval is again measured and found not to be equal to $T_3$ ($\neq T_W$), thereby indicating that the $V_3$ pulse was of insufficient energy to effectuate capture, and that the backup pulse, $V_B$, was responsible for capture.

Thus, it is seen that the invention assesses capture by looking for a significant change in the primary V-pulse-to-T-wave time interval $T_i$ for a series of ventricular pulse pairs, where the first pulse of each pair has decreasing energy from that of a primary or first pulse of a prior pair, and the backup pulse of each pair is always of sufficient energy to effectuate capture. A T-wave always follows the pulse pair because either the first stimulation pulse or the backup stimulation pulse will cause capture, i.e., depolarize the heart, so that a T-wave will occur as the heart repolarizes.

Figure 3:
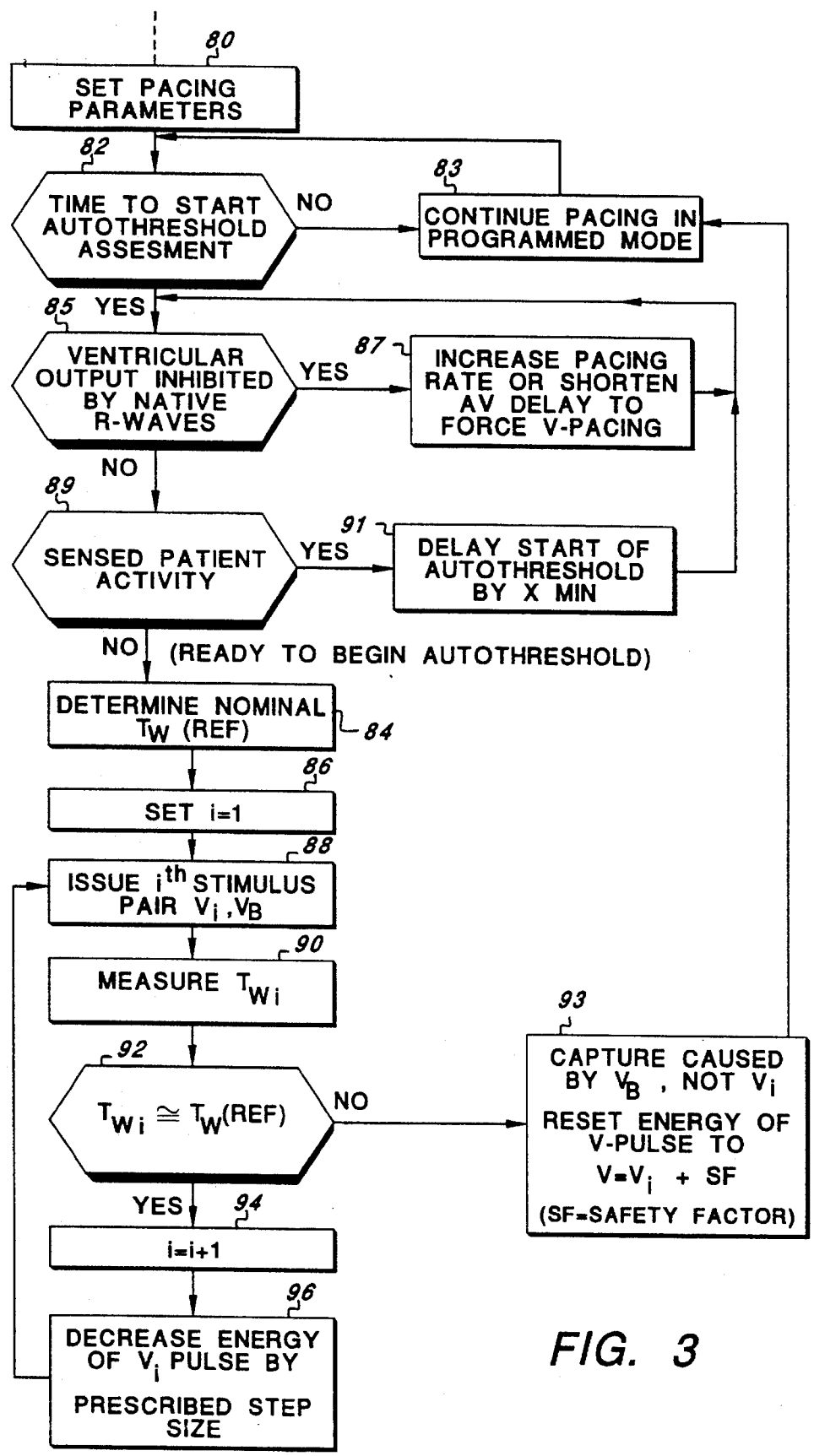
FIG. 3 is a flow chart that illustrates the method of the present invention conceptualized in FIG. 2.

The autothreshold process illustrated in FIG. 2 may advantageously be carried out within an implantable pacemaker using a method as shown in the flow chart of FIG. 3. Such method not only determines the threshold, but automatically sets the energy of the pacing stimulus at a level that is just above the determined threshold, thereby proving an autocapture feature within the pacemaker. (In the flow chart of FIG. 3, each main step of the method is depicted in a "box" or "block", with each block having a reference numeral assigned thereto for reference purposes.)

Turning to FIG. 3, it is assumed that the pacemaker is operating in a desired programmed mode, and that all of the pacing parameters needed by the pacemaker to operate in its desired program mode have been set (block 80). In addition to conventional pacing parameters, such parameters would include, for purposes of the present invention, a definition of how much the primary V-pulse is decreased in energy with each pulse pair (V-pulse decrement step size), how often the autothreshold assessment process is to be invoked (e.g., four times a day), as well as a safety factor, SF. The safety factor SF defines how much above the determined capture threshold the ventricular stimulus energy is to be set. Also, the frequency at which the autothreshold mode is to be invoked can be specified, e.g., once a day, four times a day, etc.

Assuming, then, that all of the pacing parameters have been set (block 80), a first determination is made as to whether it is time to start the autothreshold assessment process (block 81). Typically, autothreshold will start automatically at a specified frequency, e..g, once or twice every 8–12 hours, or 3–6 times every day. Also, the autothreshold routine may be triggered by command from an external programmer, or upon the occurrence of certain events within the pacemaker. If it is not time to commence autothreshold (NO branch of block 82), then the pacemaker simply continues to pace in its programmed mode (block 83).

If it is time to start the autothreshold routine (YES branch of block 82), then a first step is to verify that the proper conditions exist to accurately perform the autothreshold assessment routine. In general, such conditions require that the pacemaker be engaged in ventricular pacing (generating V-pulses) at a rate that is stable (e.g., when the patient is at rest). To verify the that such conditions are present, a determination is made as to whether the ventricular output is inhibited by naturally occurring R-waves (block 85). If naturally occurring R-waves are inhibiting V-pulses from being generated (YES branch of block 85), then some action must be taken to ensure ventricular pacing, i.e., to force the pacemaker to generate V-pulses. Typically, this is done by either increasing the pacing rate if the pacemaker is a single chamber pacemaker, or by shortening the AV delay if the pacemaker is a dual chamber pacemaker (block 87). Such action(s) should force ventricular pacing (NO branch of block 85). Other actions may be taken to achieve the same result: ventricular pacing.

Once ventricular pacing has been achieved, then a determination is made as to whether there is sensed patient activity (block 89). Sensed patient activity can readily be determined if the pacemaker is a rate-responsive pacemaker by simply checking the sensor-indicated-rate (SIR) signal generated by the pacemaker's physiological sensor. If the pacemaker is a dual chamber pacemaker, capable of sensing naturally occurring P-waves, patient activity may also be sensed by simply looking at the P-wave rate. If the P-wave rate is high, e.g., greater than 90–100 pulses per minute (ppm), then that indicates the patient is probably exercising (or engaging in some other not-at-rest activity). If patient activity is sensed (YES branch of block 89), then that suggests the patient is not at rest. As such, the autothreshold assessment procedure is delayed by x minutes (block 91), where x may be, e.g., 5–10 minutes, during which delay the pacemaker continues to operate in its programmed mode. At the conclusion of the delay of x minutes, the pacer again determines in naturally occurring R-waves are inhibiting V-pulses (block 85), and the process repeat. If patient activity is not sensed (NO branch of block 89), then the proper conditions for performing the autothreshold assessment process have been verified and the autothreshold procedure begins.

A first step in the autothreshold assessment procedure, once the proper conditions for its use have been verified, typically involves determining a nominal V-pulse-to-T-wave time period (block 84), which time period is referred to as $T_W$. Such nominal $T_W$ may be determined using any suitable technique. To determine $T_W$ it is necessary that the pacemaker issue V-pulses each cardiac cycle. It is also preferred that $T_W$ be determined when the cardiac rhythm is relatively stable. Thus, it is preferred that $T_W$ be determined while the patient is at rest. Such conditions have already been assured from the preceding verification steps. E.g., the pacemaker's AV delay has been shortened by a prescribed amount, e.g., to msec, and the SIR rate, or P-wave rate, has been checked to verify the patient is at rest. Other techniques for assuring ventricular pacing are described below. Once ventricular pacing is assured, the $T_W$ time interval is measured for a prescribed number of paced cycles, e.g., 3 to 10. An average $T_W$ may then be computed. This average or nominal $T_W$ is thereafter used as a reference time interval against which V-pulse-to-T-wave time intervals measured during the autothreshold routine may be compared.

After the nominal $T_W$ has been determined, an index pointer i is initialized (block 86), e.g., i is set equal to one. Then, the ith ventricular stimulus pair is issued (block 88), i.e., a primary pulse, $V_i$, followed by a backup stimulus, $V_B$, separated in time by a time $t_S$, where $t_S$ is selected to be less than the refractory period of the heart. It is important that the backup stimulus $V_B$ have an energy level sufficient to cause capture, and that the primary stimulus $V_i$ for the first or initial pulse pair also have an energy level sufficient to cause capture. An easy way to achieve this goal is simply to set the first primary pulse $V_1$ of the first pulse pair to be equal to the backup pulse, $V_B$. Then, after issuing the ith pulse pair, the time period from the primary pulse $V_i$ of the pulse pair to the resulting T-wave, $T_{Wi}$, is measured (block 90). This measured time $T_{Wi}$ is then compared (block 92) to the reference value of $T_W$ previously determined in block 84. If the two times are approximately equal, i.e., if $T_W \approx T_{Wi}$ (which corresponds to the YES branch of block 92), then that signifies that the primary pulse $V_i$ of the pulse pair is the pulse that captured the ventricular tissue. Accordingly, the pointer is incremented (block 94), the energy of the $V_i$ pulse is decreased by the programmed step size (block 96), and at the appropriate time, i.e., at the beginning of the next pacing cycle, another pulse pair is issued (block 88).

In the above manner, then, a series of ventricular pulse pairs are issued, with the primary or first pulse of each pair starting with an energy sufficient to capture the ventricles, but having a decreasing energy each time a new pulse pair is issued, and with the backup pulse of each pair having a fixed energy sufficient to capture the ventricles (blocks 88, 90, 92, 94 and 96). Eventually, the energy of the leading pulse of each pulse pair will drop below the capture threshold. When this happens, $T_{Wi}$ will not be equal to the reference time interval $T_W$, but will be substantially greater than $T_W$ (NO branch of block 92) because capture will be caused by the backup pulse $V_B$, rather than the leading pulse, $V_i$. Hence, $T_{Wi}$ will be roughly equal to $t_S+T_W$, where $t_S$ is the time interval between $V_i$ and $V_B$. If $t_S$ is equal to 60–100 msec, then the measured time $T_{Wi}$ from the leading pulse $V_i$ to the T-wave will thus be 60–100 msec longer than the reference V-pulse-to-T-wave time interval. The capture threshold is thus determined to be just above the energy of the current $V_i$ pulse. Hence, the energy of the V-pulse may be reset to a value that is equal to the energy of the current $V_i$ pulse plus the safety factor (block 93). With the energy of the V-pulse thus reset, the operation of the pacer can then continue in accordance with the programmed mode (block 83).

It is noted that in many instances, the invention may be practiced simply by looking for a significant change in the ventricular-stimulus-to-T-wave time interval, $T_{Wi}$, as the energy of the first pulse of a series of pulse pairs is systematically decreased. When thus practiced, it is not necessary to first measure a nominal (or average) $T_W$. All that is required is to make sure the leading pulse of the first pair of pulses is above the capture threshold, measure $T_{WI}$ for the first pulse pair, and then continue issuing additional pulse pairs, with the leading pulse being systematically decreased in energy, and simply look for a significant change in $T_{Wi}$, where a significant change will be roughly the time interval $t_S$ that separates the backup stimulus from the leading or primary stimulus, e.g., 60–100 msec.

It should be noted that because the invention relies on a change in the stimulus-to-T-wave time interval to signal that the capture threshold has been reached, it is not necessary that the time interval measurements always be made from the leading V-pulse of each pulse pair to the T-wave. All that is required is that such time measurements always be made from the same reference point within the pacing cycle. For example, the time interval from the backup pulse $V_B$ to the T-wave could just as easily be monitored after each pulse pair. So long as the leading pulse is the one that causes capture, the $V_B$-to-T-wave time interval will assume one value (shorter than $T_W$ by approximately $t_S$). As soon as the leading pulse no longer causes capture, then the $V_B$-to-T-wave time interval will assume another value ($\approx T_W$), thereby signaling that the capture threshold has been crossed.

Figure 4:
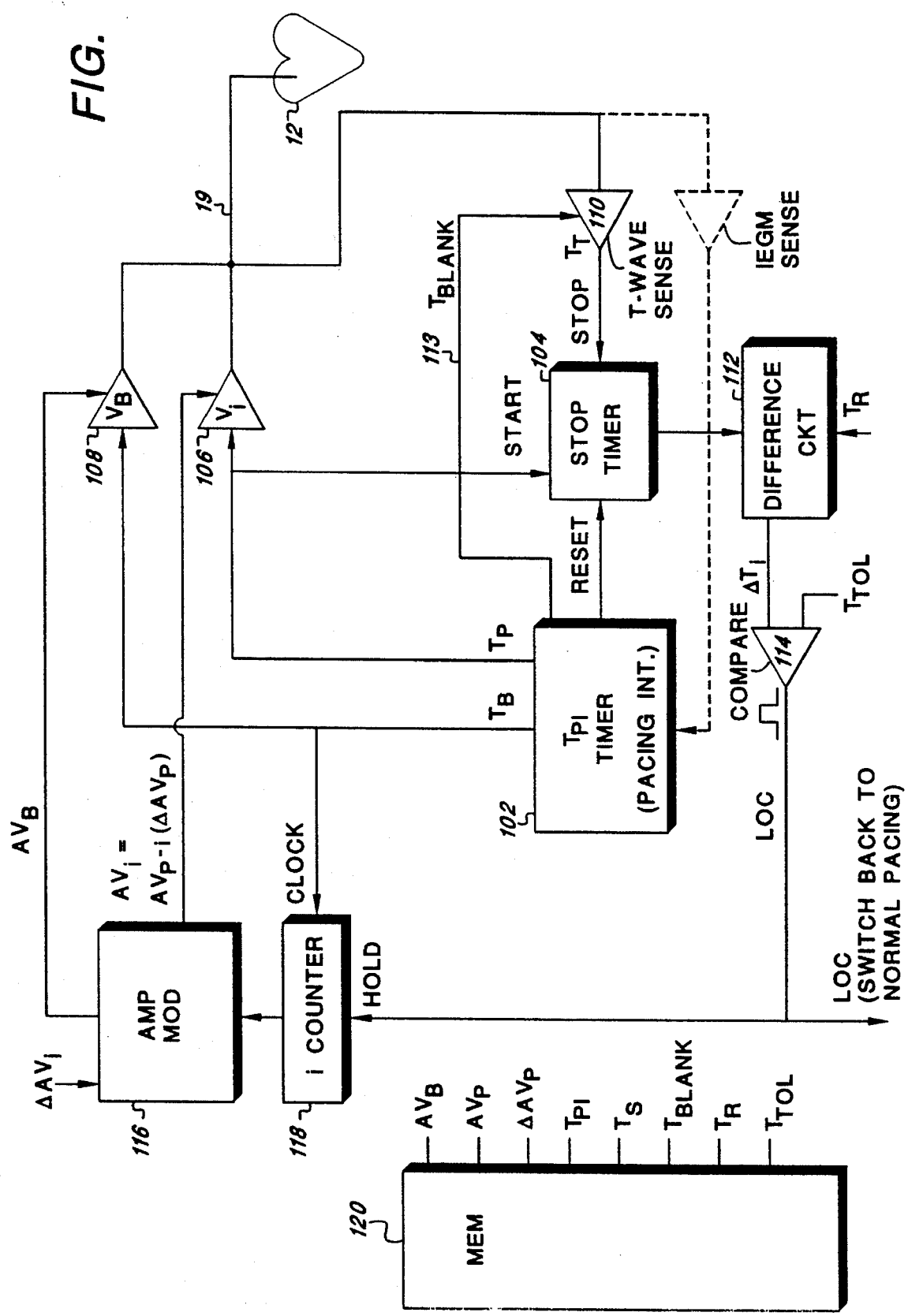
FIG. 4 is a functional block diagram that illustrates, in accordance with one embodiment, the components of a pacing system used to carry out the invention.
Figure 5:
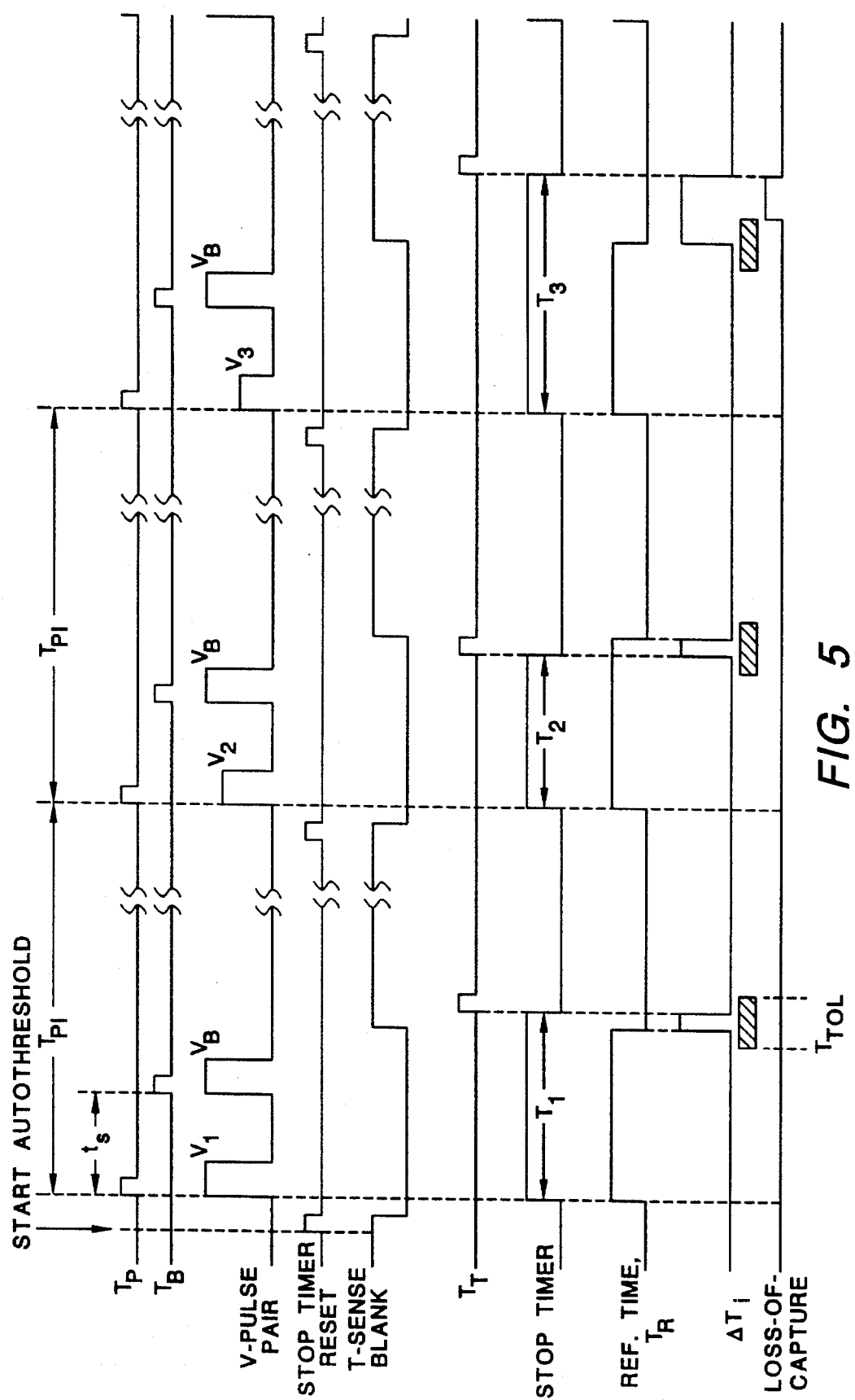
FIG. 5 is a timing diagram that illustrates the operation of the pacing system of FIG. 4.

Turning next to FIGS. 4 and 5, there is shown a functional block diagram (FIG. 5) that illustrates, in accordance with one embodiment, the components of a pacing system used to carry out the invention, and a timing diagram (FIG. 6) that illustrates the operation of such a pacing system. It is noted that the block diagram of FIG. 4 does not include all of the components of an implantable pacemaker. It only includes those needed to practice the invention in addition to the conventional components of a pacemaker. Reference should be made to FIG. 1 above, for example, or to FIGS. 6–8 below, for a more complete view of all of the components of an implantable pacer. It should also be pointed out that the block diagram of FIG. 4 is functional, meaning that the various blocks that are shown teach the function that needs to be carried out. Numerous different types of circuits, including dedicated hardware circuits and programmed-controlled processor circuits (e.g., a microprocessor), could be fashioned by those skilled in the art in order to carry out the desired functions of the invention that are taught in FIG. 4.

As seen in FIG. 4, in order to practice the present invention, the pacemaker includes a first timer 102 that sets or defines the basic pacing interval $T_{PI}$ of the pacemaker. This first timer 102 is labeled the "$T_{PI}$ Timer" in FIG. 4. As is seen in the timing waveform diagram of FIG. 5, the $T_{PI}$ Timer defines the pacing interval by issuing a $T_P$ pulse every $T_{PI}$ seconds, where $T_{PI}$ may be, e.g., 800 milliseconds (corresponding to a pacing rate of 75 bpm). The $T_{PI}$ Timer 102 also issues a $T_B$ pulse during the pacing interval that follows the $T_P$ pulse by a prescribed separation time $t_S$. The value of $t_S$ may be, e.g., 60–100 milliseconds. The $T_P$ pulse is used as a trigger pulse that is applied to pulse amplifier 106. Similarly, the $T_B$ pulse is used as a trigger pulse that is applied to pulse amplifier 108. The pulse amplifiers 106 and 108 generate the $V_i$ and $V_B$ pulses, respectively, when triggered by the $T_P$ and $T_B$ pulses. The amplitude (or energy content) of the pulses thus generated is controlled by an amplitude modulator 116. The amplitude modulator 116 generates two signals: (1) an $AV_i$ signal that defines the amplitude of the $V_i$ pulse generated by the $V_i$ amplifier 106; and (2) an $AV_B$ signal that defines the amplitude of the backup pulse $V_B$. The amplitude modulator is controlled, in part, by an pulse-pair index counter, or "i counter", 118. The counter 118 is incremented once each time a pair of V-pulses is generated, e.g., by counting the number of $T_B$ trigger pulses that are issued by the $T_{PI}$ counter 102. Hence, the parameter or flag "i" keeps track of how many pulse pairs have been issued.

Also included in the pacemaker is a "Stop Timer" 104. The Stop Timer 104 performs the same function as a "stop watch", i.e., it measures the time interval from when a start pulse is received to when a stop pulse is received. As shown in the timing diagram of FIG. 5, the $T_{PI}$ timer 102 resets the Stop Timer 104 at a time during the pacing cycle that is just prior to issuing the $T_P$ pulse of a $T_P$-$T_B$ pair. The Stop Timer 104 is started by the $T_P$ pulse. The Stop Timer is stopped by a $T_T$ pulse. The $T_T$ pulse is generated by a T-wave sense amplifier 110.

The T-wave sense amplifier 110 is coupled to a lead 19 that connects with the ventricle of a heart 12 of the pacemaker patient so as to detect the occurrence of a T-wave. In order to protect the T-wave sense amplifier 110 from the large ventricular pulse pair $V_i$-$V_B$, a blanking signal, $T_{BLANK}$, is generated by the $T_{PI}$ timer 102 during that portion of the pacing cycle when the pulse pair $V_i$-$V_B$ is present, and for several, e.g., 10–20 msec, thereafter. The blanking signal thus serves the function of enabling or disabling (and protecting) the T-wave sense amplifier 110. When enabled after the $T_{BLANK}$ signal has expired, the T-wave sense amplifier thus monitors the ventricle for the occurrence of a T-wave. When a T-wave is sensed, the T-wave sense amplifier generates the $T_T$ pulse. The presence of the $T_T$ pulse thus signifies that a T-wave has been sensed.

The Stop Timer 104 thus measures the time interval $T_i$ between the $T_P$ pulse and the $T_T$ pulse during each pacing cycle wherein a pulse pair is generated. That is, the Stop Timer 104 measures the time between the leading pulse of each pulse pair and a T-wave. As seen in the timing diagram of FIG. 5, a first time interval $T_1$ is measured corresponding to the first pulse pair $V_1$-$V_B$; a second time interval $T_2$ is measured corresponding to the second pulse pair $V_2$-$V_B$; and a third time interval $T_3$ is measured corresponding to the third pulse pair $V_3$-$V_B$.

The time intervals $T_i$ measured by the Stop Timer 104 are compared against a reference time interval $T_R$ by a difference circuit 112. The difference circuit 112 generates an output signal $\Delta T_i$ that represents the time difference between the measured time interval $T_i$ and the reference time interval $T_R$. The determined time difference $\Delta T_i$ is then compared against a reference tolerance signal, $T_{TOL}$, to determine if it exceeds a prescribed tolerance. If it does not, then no loss-of-capture (LOC) signal is generated. If it does, then a LOC signal is generated. To illustrate, in FIG. 5, the first measured time interval $T_1$ is approximately equal to the reference time interval $T_R$, so the difference signal $\Delta T_1$ is a very narrow signal that is less than the prescribed tolerance $T_{TOL}$. Hence, no LOC signal is generated. Similarly, the second measured time interval $T_2$ is approximately equal to the reference time interval $T_R$, so the difference signal $\Delta T_2$ is also a very narrow signal that is less than the prescribed tolerance $T_{TOL}$. Hence, again no LOC signal is generated. However, the third measured time interval $T_3$ is substantially greater than the reference time interval $T_R$, and the difference signal $\Delta T_3$ is thus a large (wide) signal that exceeds the prescribed tolerance $T_{TOL}$. Hence, a LOC signal is generated, indicating that loss-of-capture occurred for the third pulse pair, when the leading stimulation pulse was $V_3$.

The LOC signal is used by the pacemaker circuits to cease the autothreshold mode. The LOC signal may also be applied to the "i counter" 118 to hold the count therein. This count is then used by the amplitude modulator 116, or other processor, to determine at what energy level capture was lost. For example, the amplitude modulator 116 may be programmed to decrease the amplitude of the leading pulse of each pulse pair by a prescribed step size $\Delta AV_P$. Thus, the amplitude of the leading pulse of each pulse pair has an amplitude that may be expressed as:

$$AV_i = AV_P - i(\Delta AV_P)$$

where $AV_P$ is the initial amplitude of the first pulse. Hence, once capture is lost, it is a simple matter to determine the amplitude of the leading pulse that lost capture (which amplitude is just below the capture threshold) by simply knowing the number, or index i, of the pulse pair having such loss-of-capture leading pulse, and then using the above relationship to determine the amplitude. The index is simply the count held in the counter 118.

Other techniques may also be used to determine the energy at which capture is lost in addition to, or in place of, the technique described above, or computing the loss-of-capture energy based on how many times the leading pulse pair is decremented by a fixed energy increment. For example, the amplitude of the leading pulse of each pulse pair could be held in a register (if digital), or stored on a capacitor (if analog), and updated each time a new pulse pair is generated. Then, when a LOC signal is generated, such amplitude could be retrieved and used as an indicator of the loss-of-capture threshold.

Once the loss-of-capture threshold is known, it then becomes a straightforward task to invoke an autocapture mode. In an autocapture mode, the energy of the V-pulse is set to a value that is a prescribed safety factor (SF) above the determined loss-of-capture threshold.

In the above example, the energy content of the leading stimulus of the pulse pair is adjusted by decreasing its amplitude. Adjusting amplitude is only one way to control the energy within an electrical stimulus. Energy can also be adjusted by changing the pulse width of the stimulus, or by changing both the amplitude and pulse width.

As further seen in FIG. 4, the operating parameters needed to operate the pacemaker in the autothreshold and/or autocapture modes are preferably stored in a memory 120 of the pacemaker. Such operating parameters may then be programmed, using conventional pacemaker programming techniques, in order to set them at appropriate values for a given patient. The operating parameters typically include:

$AV_B$, the amplitude of the backup stimulation pulse; $AV_P$, the amplitude of the leading stimulation pulse of the first pulse pair (which may be equal to $AV_B$); $\Delta AV_P$, the step size by which the leading pulse amplitude is decreased each pulse pair; $T_{PI}$, the basic pacing interval (which may be generated by other pacing circuits); $T_{BLANK}$, the T-wave sense amplifier blanking period; $t_S$, the separation between the leading pulse and the backup pulse of each pulse pair; $T_R$, the reference time interval; and $T_{TOL}$, the amount of variation or tolerance that may exist between the measured time interval $T_i$ and the reference time interval $T_R$ before a LOC condition is declared. The value of $T_R$, as indicated above, may be determined based on an average of the stimulus-to-T-wave time measured during 3–10 previous paced cycles.

Again, it is emphasized that which is shown in FIG. 4 is functional. Those skilled in the art will be able to readily fashion numerous types of circuits and programmed processors that carry out the functions described. For example, all but the $V_i$ and $V_B$ pulse generators 106, 108, and the T-wave sense amplifier 110, may readily be incorporated within a digital controller circuit, or programmed microprocessor.

The pulse generators 106, 108 may be of conventional design, and will typically be the same ventricular pulse generator 20 used by the pacemaker 10 (FIG. 1). In this regard, note that it is not necessary that separate pulse generators be used to generate the pulse pair, although separate pulse generators may be used, if desired. Rather, a single pulse generator may be used that is triggered twice, once by the $T_P$ pulse, and once $t_S$ seconds later by the $T_B$ pulse.

The T-wave sense amplifier 110 may likewise be of conventional design, i.e., the type of sense amplifier used to sense the ventricular depolarization (R-amp 24 in FIG. 1). Preferably, however, a separate amplifier should be used for the T-wave amplifier 110 than is used to sense R-waves or P-waves, as the bandwidth of the T-wave amplifier should be somewhat wider than the bandwidth of an R-wave or P-wave amplifier. Further, by using a separate T-wave amplifier, the T-wave can be sensed with any lead configuration: unipolar, conventional bipolar (tip-to-ring), or modified bipolar (ring-to-case, or tip- to-case).

Advantageously, the present invention may be used with almost any type of pacemaker. If the pacemaker with which the present invention is used is a rate-responsive (RR) pacemaker, i.e., one that uses one or more physiological or other sensors in an attempt to sense the metabolic needs of the patient, and generates a sensor-indicated-rate (SIR) signal from the information thus sensed to vary the basic pacing interval of the pacemaker, then the autothreshold feature of the present invention should preferably be performed only when the patient is at rest. Thus, a preliminary step in carrying out the invention with a rate-responsive pacemaker is to look at the SIR signal, and suspend the autothreshold mode of the invention until the SIR signal indicates the patient is at rest.

As mentioned previously, for the autothreshold routine to be successfully invoked, it is necessary to be in a ventricular pacing mode, i.e., to be in a mode where V-pulses are generated to pace the ventricles, as opposed to monitoring naturally occurring R-waves and only providing a V-pulse occasionally. To insure ventricular pacing, it is preferred that the pacer include the ability to measure the natural heart rate (a feature commonly available in many RR pacers). If such a measurement reveals that the heart rate is, e.g., 75 bpm, but the pacing rate is only set to 60 bpm (which means that no pacing would be occurring), then the present invention preferably includes the ability to increase the basic pacing rate to a value greater than the measured heart rate, e.g., to 76 bpm, to assure that ventricular pacing will occur. If an RR pacer is used, then this adjustment of the basic pacing interval may be linked to checking the SIR signal to determine if the patient is active (which, if active, would account for the faster heart rate). If not active, then the pacer would automatically adjust the pacing rate to a value greater than the measured rate.

Alternatively, rather than adjusting the overall basic pacing interval (which is made up of a V-to-A interval, or VA interval, plus an A-to-V delay, or AV delay) in order to assure ventricular pacing, the AV delay of the pacer can be shortened, while maintaining the overall pacing interval at the same value (i.e., increasing the VA interval by approximately the same amount as the AV delay is shortened).

Moreover, if operating in a pacer mode where P-waves are tracked, the P-wave or atrial rate may be monitored. If there is a high atrial rate, and if the SIR signal indicates a fast rate, then the autothreshold feature of the present invention should be suspended until the patient is at rest (i.e., until the atrial rate slows down). However, should the SIR signal indicate the patient is at rest at the same time that the atrial rate is high (as might occur, for example, if the SIR signal is based on sensed activity of the patient, and the patient is at rest while experiencing an emotionally charged event), then either the AV delay may be shortened, and/or the basic pacing interval may be shortened, in order to assure that pacing occurs in the ventricle before starting the autothreshold routine.

Indeed, there are numerous and varied techniques that may be used to assure ventricular pacing, any of which could be used with assessing autothreshold in accordance with the present invention. Whatever technique is employed, and with whatever type of pacing mode, the autothreshold routine of the present invention is carried out, when needed (which should be infrequently, e.g., 1–4 times per day) by simply: (1) issuing a series of stimulus pulse pairs, with the leading pulse of each pair starting at an energy level sufficient to effectuate capture, and decreasing in energy thereafter in an ordered manner, and with the trailing pulse of each pair starting and remaining at an energy level sufficient to effectuate capture; and (2) measuring, from a constant reference point, e.g., the first pulse of each pulse pair, the time interval to the T-wave of each pacing cycle. As long as the time-to-T-wave interval stays relatively constant as the energy of the leading pulse of each pulse pair is decreased, the capture threshold has not yet been reached by the leading pulse. As soon as the time-to-T-wave interval significantly lengthens, the capture threshold has been crossed by the leading pulse, and the energy of the leading pulse at the instant of cross-over, i.e., at the instant when the measured time-to-T-wave interval significantly increases, may be used as an indicator of the capture threshold.

Figure 6:
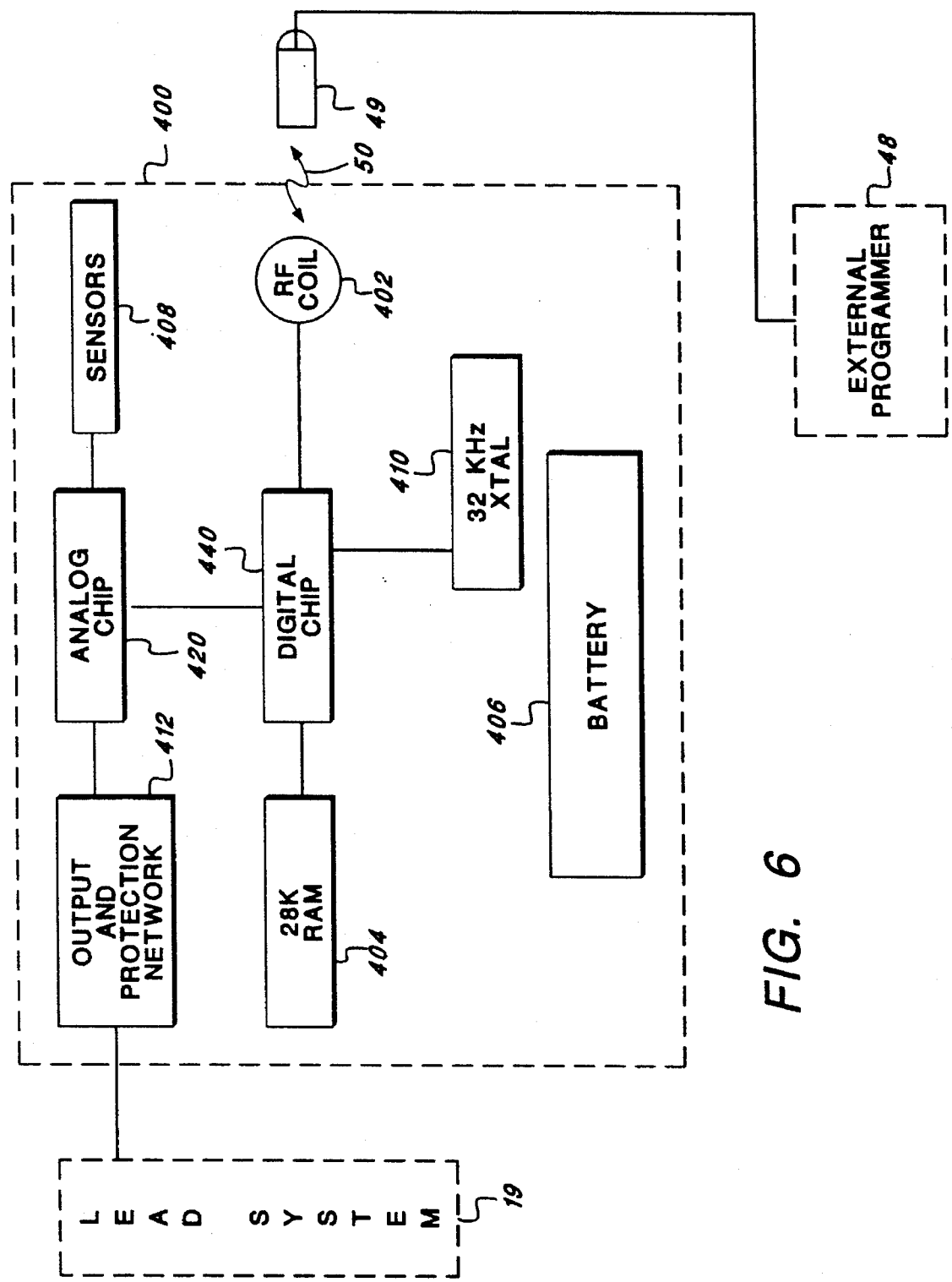
FIG. 6 is a block diagram of a preferred pacemaker with which the present invention may be used.

Referring next to FIG. 6, there is shown a block diagram of the main hardware components of a preferred pacemaker with which the present invention may be used. The system includes the external programmer 48, the implantable pacemaker 10, and the lead system 19. The lead system 19 includes conventional atrial and ventricular leads and electrodes, as described previously. The lead system 19 may also include an oxygen sensor lead, which lead contains an LED-detector assembly used to measure the oxygen content of the blood. Such a lead is described, e.g, in U.S. Pat. No. 4,815,469, incorporated herein by reference.

The external programmer 48 includes a telemetry head 49 that is positioned proximate the implantable pacemaker 10 whenever a communication link 50 is to be established between the pacemaker 10 and the external programmer 48. The external programmer may be of conventional design, as described, e.g., in U.S. Pat. No. 4,809,697, incorporated herein by reference.

The components of the pacemaker 10 are housed within a suitable sealed case or housing 400 (which case or housing is represented in FIG. 6 by the dashed line 400). The case 400 is preferably a titanium metal case. The components within the case 400 include an RF coil 402, a memory chip 404, a battery 406, one or more sensors in a sensor circuit 408, a crystal 410, an output/protection network 412, an analog chip 420 and a digital chip 440.

The battery 406, which is by volume the largest component within the pacemaker 10, may be of conventional design, and is a lithium battery that provides operating power to all of the electronic circuits within the pacemaker. The RF coil 402 is used to establish the communication link 50 with the telemetry head 49. The crystal 410 is used in conjunction with a crystal oscillator circuit on the digital chip 440 (described below) to provide a stable clock frequency for the pacemaker circuits. In the preferred embodiment, the frequency of the crystal oscillator is 32 KHz, although any suitable frequency could be used. The sensor circuit 408 includes appropriate sensors used by the pacemaker as it carries out a rate-responsive pacing function. For example, in one embodiment, the sensor circuit 408 includes an accelerometer adapted to sense patient activity.

The memory chip 404 is a low-power static random access memory (RAM) chip wherein the operating parameters, e.g., control variables, of the pacemaker may be stored, and wherein sensed data may be stored, as required. The analog chip 420 and the digital chip 440 contain the main processing and control circuits of the pacemaker. These chips are advantageously designed to minimize the number of components needed external thereto for operation of the pacemaker. The analog chip 420 interfaces with the lead system 19 through the output and protection network 412, which network includes output capacitors, appropriate feed-through connectors to allow electrical connection through the hermetically sealed case, and the like, as are commonly used in implantable medical devices.

Figure 7:
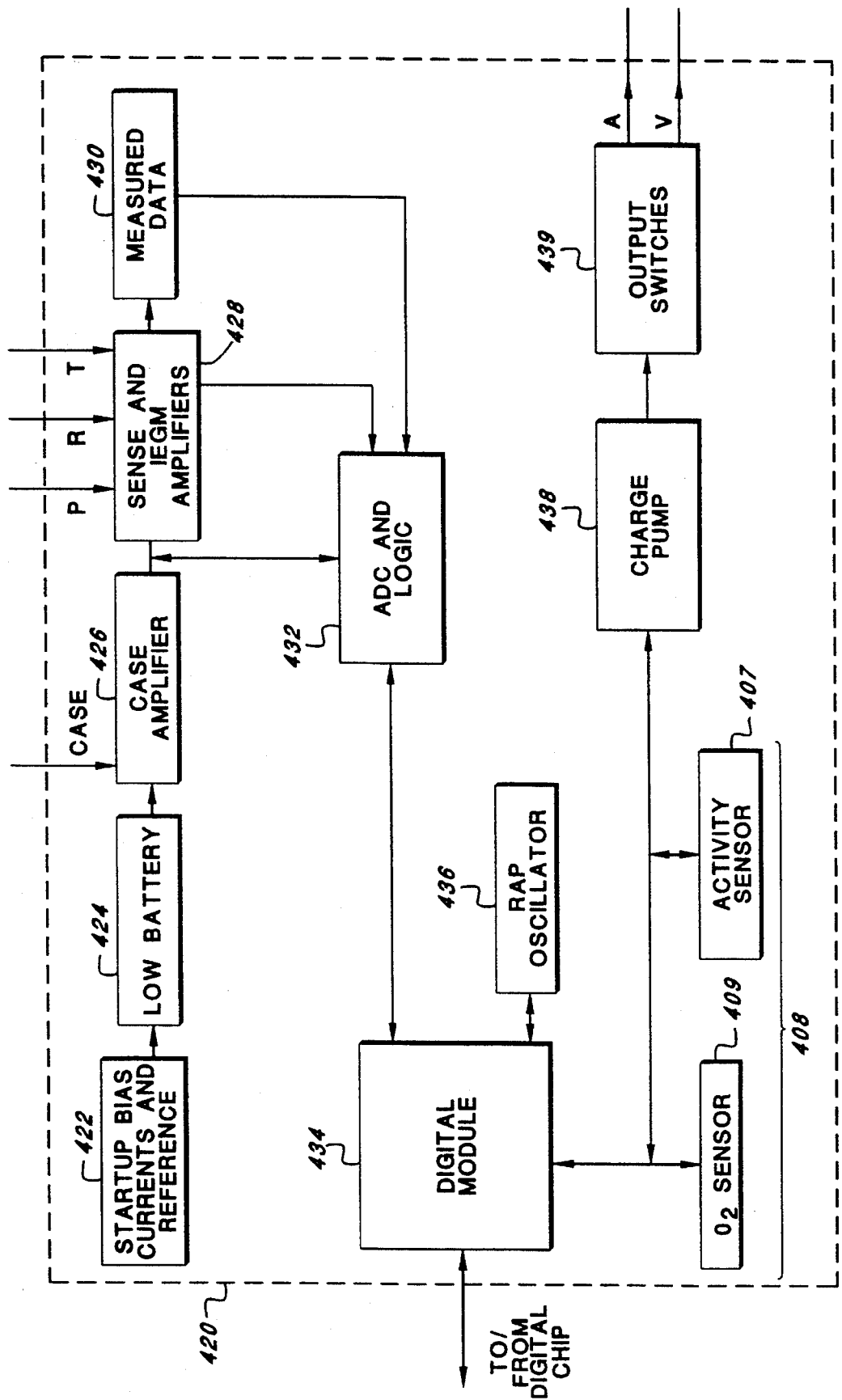
FIG. 7 is a block diagram of the analog chip of the pacer of FIG. 6.

Referring next to FIG. 7, a block diagram of the analog chip 420 is shown. The analog chip contains all the necessary sub-systems and modules to interface to the lead system 19 and the digital chip 440. For example, a startup/bias-current/reference module 422 contains the power-up signals used to initialize the pacer circuit when the battery is first applied. A low battery module 424 detects four voltage levels of the battery voltage for determining the battery status. A case amplifier 426 generates a CASE bias voltage that is used as a reference for the sense and IEGM (intracardiac electrogram) amplifier module 428. The module 428 includes the P-wave amplifier 22, the R-wave amplifier 24, and the T-wave amplifier 110, described above in FIG. 1. A measured data module 430 measures the battery voltage and current and other analog parameters of the pacing system. An ADC and Logic module 432 includes an analog-to-digital converter and timing logic that are used to convert the analog signals of the pacemaker in to 8-bit digital words. These digital words are then passed to a digital module 434, which module is used to generate all the basic timing and bus control functions as data is passed back and forth between the analog chip 420 and the digital chip 440.

Still referring to FIG. 7, it is seen that a Runaway Protection (RAP) circuit oscillator 436 is also coupled to the Digital Module 434. Such oscillator 436 provides an independent time base for limiting the highest pacing rate allowed by the pacemaker. Further coupled to the digital module 434 is the sensor network 408. The sensor network 408 includes appropriate sensors for sensing activity and other parameters. For example, an O2 sensor circuit 409 may be used in conjunction with the oxygen sensor lead, when used, to measure blood oxygen of the patient. An activity sensor 408 may also be used to sense patient activity as measured, e.g., by an accelerometer. A charge pump circuit 438 generates the output voltages for the stimulation pulses that are delivered to the patient's heart. A network of output switches 439 connects the charge developed by the pump circuit 438 to the output leads at the appropriate time to form the appropriate stimulation pulses.

It is thus seen that the analog chip 420 contains the necessary circuitry to sense and detect atrial or ventricular events, digitize IEGM waveforms, measured data and other various analog signals, and provide such sensed and digitized signals to the digital module 434 for use by the digital chip 440. The charge pump circuit 438 acts as a voltage doubler/tripler for high output pulse capability. The output pulse width is controlled by the output switches 439. The condition of the battery is monitored, and independent Runaway Protection is provided.

Figure 8:
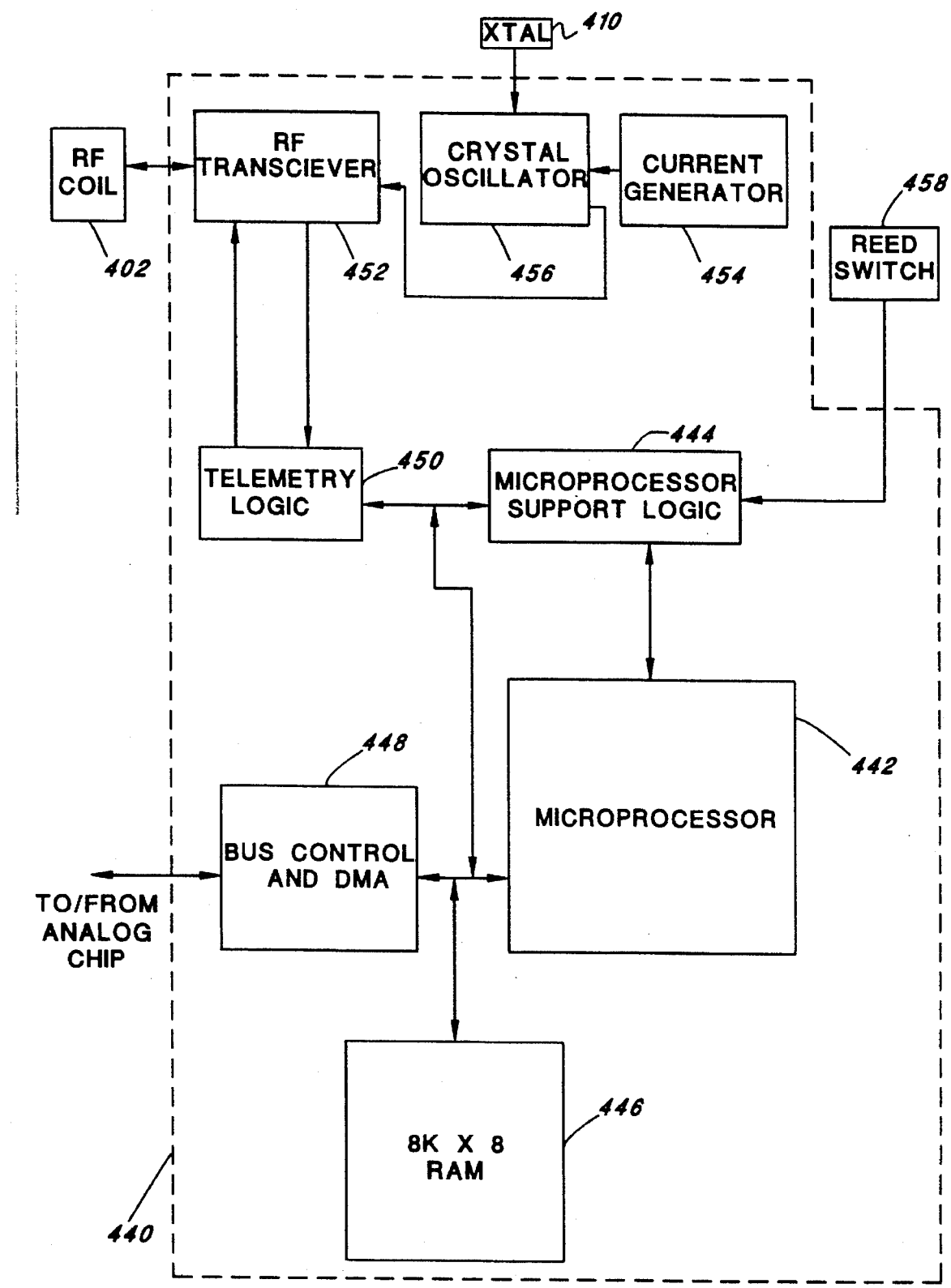
FIG. 8 is a block diagram of the digital chip of the pacer of FIG. 6.

Turning next to FIG. 8, it is seen that the main control element of the pacemaker is a microprocessor 442, which microprocessor is included within the digital chip 440. The digital chip 440 contains all the necessary logic to interface the analog chip 420 with the internal microprocessor 442. The microprocessor 442 includes a basic CPU (central processing unit) and 8K of static RAM. In addition, an 8K by 8K RAM 446 is connected to the microprocessor 442 to store data and programs. Microprocessor support logic 444, also coupled to the microprocessor 442, includes interrupt logic, timer logic, noise/sensed event logic, and magnet status logic. A bus controller 448 is further included on the digital chip 440 to provide DMA timing and control of data transfer with the analog chip 420, including timing and control of the analog-to-digital converter 432 (FIG. 7) and telemetry data. Telemetry channel logic 450 contains clock logic, IEGM and marker logic, telemetry command protocol logic, telemetry interrupt logic, error checking logic and CPU reset logic. An RF transceiver 452, coupled to the RF coil 402, transmits and receives telemetry data from the external programmer 48 through the telemetry head 49 (see FIG. 6). A crystal oscillator circuit 456, in conjunction with the crystal 410 (external to the digital chip 440) provides the crystal time base of the pacemaker system. A current generator 454 provides the bias currents for the digital chip. A reed switch circuit 458 detects the presence of a magnetic field, which magnetic field is present whenever the telemetry head 49 is in place on the patient's skin above the location where the pacemaker is implanted.

The pacemaker circuitry described in connection with FIGS. 6–8 above provides the basic functions of the pacemaker described in connection with FIG. 1, plus other pacing/sensing functions as are known in the art. For purposes of the present invention, the pacemaker circuitry of FIGS. 6–8 sets the basic timing of the pacing interval, including setting an AV interval and a VA interval. The circuitry also provides for sensing or detecting natural ventricular events (R-waves), natural atrial events (P-waves), repolarization events (T-waves), and for measuring the time interval between a paced ventricular event (V-pulse) and the resulting T-wave (i.e., for measuring the repolarization time).

As described above, it is thus seen that an implantable pacemaker is provided wherein capture can be assessed without the need to sense an evoked response immediately following an applied stimulus, and at a time when potentially interfering polarization voltages are not present at the electrode/tissue interface. Further, it is seen that the invention provides a simple capture-determining technique that does not require bipolar pacing leads, nor special low-polarization electrode materials.

While the invention herein disclosed has been described by means of specific embodiments and applications thereof, numerous modifications and variations could be made thereto by those skilled in the art without departing from the scope of the invention set forth in the claims.

What is claimed is:

1. A method of automatically assessing a capture threshold of an implantable pacemaker electrically coupled to cardiac tissue, comprising:

(a) generating a sequence of paired stimuli at a prescribed pacing rate, a leading stimulus of each pair of the paired stimuli having an adjustable energy content beginning with an energy content on one side of the capture threshold, and a trailing stimulus of each pair of the paired stimuli always having an energy content above the capture threshold;

(b) applying the sequence of paired stimuli to the cardiac tissue while adjusting the energy content of the leading stimulus toward the capture threshold;

(c) measuring a repolarization time as the length of time it takes the cardiac tissue to repolarize following each pair of the paired stimuli; and (d) defining the capture threshold to be approximately equal to the energy content of the leading stimulus of the paired stimuli that immediately precedes a substantial change in the repolarization time.

2. The method set forth in claim 1, wherein the step of generating the sequence of paired stimuli comprises generating the trailing stimulus of each paired stimuli 60 to 100 milliseconds after the leading stimulus.

3. The method set forth in claim 2, wherein the step of adjusting the sequence of paired stimuli comprises initially setting the energy content of the leading stimulus to be equal to the energy content of the trailing stimulus, and systematically decreasing the energy content of the leading stimulus by a prescribed amount thereafter.

4. The method set forth in claim 2, wherein the step of adjusting the sequence of paired stimuli comprises initially setting the energy content of the leading stimulus to a value below the capture threshold, and systematically increasing the energy content of the leading stimulus by a prescribed amount thereafter.

5. The method set forth in claim 2, wherein the step of adjusting the energy content of the leading stimulus includes changing the energy content of the leading stimulus each time a new paired stimuli is generated.

6. The method set forth in claim 1, wherein the step of defining the capture threshold comprises defining the capture threshold to be approximately equal to the energy content of the leading stimulus of the paired stimuli that immediately precedes a change in the repolarization time of at least 20%.

7. The method set forth in claim 6, wherein the step of measuring the repolarization time comprises measuring the time interval between the leading stimulus of each paired stimuli and the occurrence of a T-wave.

8. The method set forth in claim 6, wherein the step of measuring the repolarization time comprises measuring the time interval between the trailing stimulus of each paired stimuli and the occurrence of a T-wave.

9. The method set forth in claim 1, wherein the step of applying the sequence of paired stimuli to the cardiac tissue comprises applying the paired stimuli to ventricular tissue.

10. The method set forth in claim 1, wherein the step of applying the sequence of paired stimuli to the cardiac tissue comprises applying the paired stimuli to atrial tissue.

11. The method set forth in claim 1, further including:

(e) ceasing the generation of paired stimuli once the capture threshold has been defined; and (f) setting the energy of electrical stimuli generated by the pacemaker thereafter to be equal to the capture threshold plus a safety factor.

12. A method of determining capture threshold within an implantable pacemaker, the pacemaker having means for selectively generating ventricular stimuli at a rate that defines a cardiac cycle in order to evoke depolarization of ventricular muscle tissue, thereby assuring a ventricular contraction each cardiac cycle, and means for sensing a T-wave, the T-wave evidencing repolarization of the ventricular muscle tissue following depolarization thereof, the method comprising:

(a) generating a pair of ventricular stimulation pulses during each cardiac cycle, the pair of ventricular stimulation pulses comprising a primary stimulation pulse ($V_i$) followed by a backup stimulation pulse ($V_B$) within 60–100 msec of the primary stimulation pulse, the primary stimulation pulse having a first energy that decreases in accordance with a set schedule, and the backup stimulation pulse having a second energy, and wherein the second energy is an energy sufficient to capture the ventricles;

(b) measuring how long of a time interval exists between application of the primary ventricular stimulation pulse $V_i$ of each pair of ventricular stimulation pulses and the sensing of a T-wave; and (c) defining a loss of capture condition if the time interval measured in step (b) undergoes a change of approximately 60–100 msec from a prior measurement.

13. An implantable cardiac pacemaker that automatically determines a capture threshold comprising:

timing means for defining a cardiac cycle; means for generating a pair of ventricular stimulation pulses during each cardiac cycle, the pair of ventricular stimulation pulses comprising a primary stimulation pulse ($V_i$) followed by a backup stimulation pulse ($V_B$) within a time $T_S$ from the primary stimulation pulse, where $T_S$ is less than the natural refractory period of cardiac muscle tissue, the primary stimulation pulse having a first energy, and the backup stimulation pulse having a second energy, and wherein the first energy is an adjustable energy, and wherein the second energy is always an energy sufficient to capture the ventricles;

means for systematically changing the energy of the primary stimulation pulse of each pair of ventricular stimulation pulses in accordance with a prescribed schedule;

means for sensing the occurrence of a T-wave;

means for measuring a V-to-T time period, $T_i$, for each cardiac cycle during which the pair of ventricular stimulation pulses is generated, the time period $T_i$ comprising the time interval from a designated one of the pair of ventricular stimulation pulses and the occurrence of a T-wave during the same cardiac cycle; and means for monitoring the measured time period, $T_i$, and for defining a capture threshold as being approximately equal to the energy of the primary stimulation pulse during the cardiac cycle in which there is a substantial change in the measured time period $T_i$.

14. The pacemaker of claim 13, wherein $T_S$ comprises a time period of from 60 to 100 milliseconds.

15. The pacemaker of claim 13, wherein the first energy of the primary stimulation pulse is initially equal to the second energy of the backup stimulation pulse, and wherein the means for systematically changing the energy of the primary stimulation pulse comprises means for systematically decreasing the energy of the primary stimulation pulse.

16. The pacemaker of claim 13, wherein the first energy of the primary stimulation pulse is initially a low energy insufficient to capture the ventricles, and wherein the means for systematically changing the energy of the primary stimulation pulse comprises means for systematically increasing the energy of the primary stimulation pulse.

17. The pacemaker of claim 13, wherein the means for monitoring comprises means for comparing the measured time interval $T_i$ against a reference time interval $T_W$ and wherein $T_W$ comprises an average V-to-T time period for at least three consecutive paced cardiac cycles that precede the generation of the pair of ventricular stimulation pulses.

18. The pacemaker of claim 17, wherein the means for comparing defines a capture threshold only when the difference between the measured time period $T_i$ and the reference time period $T_W$ is at least $0.9 \times T_S$.

19. A capture threshold assessment system for use within an implantable pacemaker comprising:

a timer that defines a paced interval;

a pulse generator responsive to the timer that generates a pair of stimulation pulses in synchrony with the paced interval, a first pulse of the pair of pulses having a first programmed amplitude, and a second pulse of the pulse pair having a second programmed amplitude, the first and second pulses being separated by a time period $t_S$, where $t_S$ is less than a refractory period of cardiac tissue, and the second programmed amplitude being set at a high value that always causes capture;

a sense amplifier adapted to sense a T-wave, the T-wave evidencing repolarization of cardiac muscle tissue that has depolarized;

time interval measurement means for generating a timed interval within each paced interval that starts when the pulse generator generates the first stimulation pulse and stops when the sense amplifier senses a T-wave, the magnitude of the timed interval thus providing a measure of how long it takes a T-wave to occur in each paced interval following the first stimulation pulse of the pulse pair;

energy adjustment means for systematically adjusting the first programmed amplitude of the first pulse of the pair of pulses;

comparison means for comparing the measured timed interval against a reference timed interval as the energy adjustment means systematically adjusts the first programmed amplitude of the first pulse, with the reference timed interval defining a nominal delay between a stimulation pulse that causes capture and the T-wave resulting from such capture; and means for generating a loss-of-capture signal whenever the measured timed interval differs from the reference timed interval by an amount approximately equal to $t_S$.

20. The capture threshold assessment system of claim 19, wherein the energy adjustment means comprises means for initially setting the first programmed amplitude of the first pulse of the pair of pulses to value that causes capture, and means for thereafter systematically decreasing the first programmed amplitude.

* * * * *